United States Patent [19]

Redwine

[11] 4,233,252
[45] Nov. 11, 1980

[54] BUTADIENE CHLORINATION PROCESS
[75] Inventor: Terry W. Redwine, La Place, La.
[73] Assignee: E. I. Du Pont de Nemours and Company, Wilmington, Del.
[21] Appl. No.: 823,096
[22] Filed: Aug. 9, 1977
[51] Int. Cl.³ .............................................. C07C 21/09
[52] U.S. Cl. .................................................... 570/231
[58] Field of Search .................................... 260/654 H
[56] References Cited
U.S. PATENT DOCUMENTS

| | | | |
|---|---|---|---|
| 1,286,353 | 12/1918 | Lacy | 260/662 R |
| 2,299,477 | 10/1942 | Hearne et al. | 260/654 H |
| 4,049,729 | 9/1977 | Otto et al. | 260/654 H |

FOREIGN PATENT DOCUMENTS 519691  12/1955  Canada ................................ 260/654 H

*Primary Examiner*—Delbert E. Gantz
*Assistant Examiner*—Joseph A. Boska

[57] ABSTRACT

An improved process for the continuous chlorination in vapor phase of butadiene to a mixture of dichlorobutenes at a temperature about 90°–250° C., wherein chlorine is premixed with a portion of butadiene and introduced at one end of a tubular reactor, while the remainder of the butadiene, which is used in a large excess, is introduced at one or more points downstream from the point of introduction of the chlorine-butadiene mixture, the temperature and volume of this additional butadiene being sufficient to effectively cool the reacting mixture so that the maximum temperature in the reactor does not exceed about 250° C. but does not fall downstream from the butadiene injection point below about 130° C.

9 Claims, 1 Drawing Figure

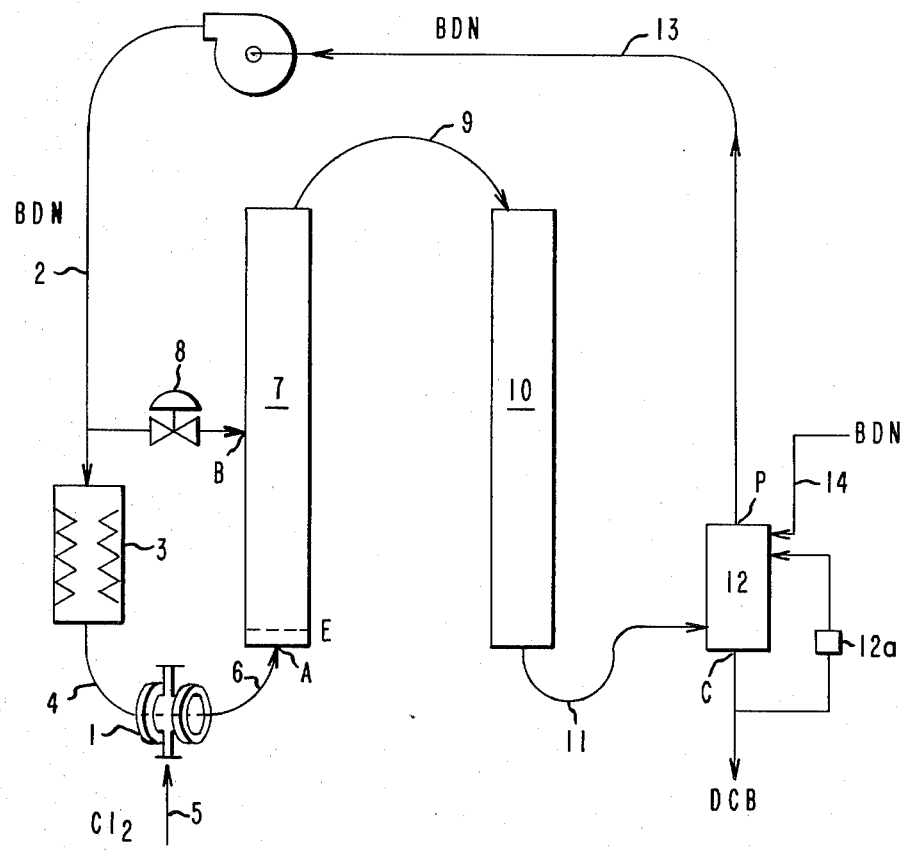

BUTADIENE CHLORINATION PROCESS

BACKGROUND OF THE INVENTION

This invention relates to an improvement in a continuous process for the chlorination of butadiene to a mixture of dichlorobutenes.

Dichlorobutenes are important intermediates in the synthesis of chloroprene, which is the key monomer in the manufacture of neoprene rubbers as well as of hexamethylenediamine, which is one of the starting materials in the synthesis of nylon 66 polyamides.

Vapor phase chlorination of butadiene to dichlorobutenes is well known. One commercial process is described in British Pat. No. 1,290,607 to E. I. du Pont de Nemours and Company. This process is carried out under substantially adiabatic conditions in a tubular reactor. Butadiene and chlorine vapor are combined in a molar ratio of about 5:1 to 50:1 (preferably, 8:1 to 30:1) at a temperature of about 70°–175° C. and introduced into a reactor maintained at a temperature below 250° C. The product stream contains dichlorobutenes, butadiene, trichlorobutenes and tetrachlorobutanes. This process is capable of giving high yields of dichlorobutenes, usually in excess of 90%, normally about 91–93%.

Because of the large scale of industrial operations in which dichlorobutenes are produced, there is a considerable economic incentive in improving the yields of dichlorobutenes still further; or, in the alternative, in increasing the reactor capacity without a loss of yield. Mere increase of the feed rates results in a yield loss.

SUMMARY OF THE INVENTION

According to this invention, there is now provided an improved process for the continuous chlorination of butadiene to a mixture of dichlorobutenes, the process comprising the following steps:

1. Premixing chlorine with a portion of the total butadiene, the mole ratio of butadiene to chlorine in the mixture being at least 3:1 but no more than 30:1, and the temperature of the mixture being at least 90° C. but no more than 200° C.;
2. Continuously introducing the chlorine-butadiene mixture at one end of a tubular reactor maintained above 90° C., while introducing the remainder of butadiene into the reactor at at least one point downstream from the injection point of the chlorine-butadiene mixture, the temperature of butadiene at each injection point being lower than the temperature of the reacting mixture at that point, both the temperature and the volume of this additional butadiene being adequate to prevent the internal temperature in the reactor from exceeding about 250° C. or falling downstream from any butadiene injection point below about 130° C., and,
3. Recovering dichlorobutenes from the reactor effluent.

THE DRAWING

The drawing is a schematic representation of the improved process of the present invention.

DETAILED DESCRIPTION OF THE INVENTION

The process of the present invention, like the prior commercial process described in British Pat. No. 1,290,607, uses an excess of butadiene as a heat transfer medium, to moderate the reaction temperature. The improvement of this invention resides principally in dividing butadiene into portions which are added incrementally downstream from the injection point of the chlorine-butadiene feed mixture.

Referring now to the drawing, 1 is a mixing tee in which chlorine and butadiene are mixed in the correct ratio. Butadiene is pumped through line 2, preheater 3, and line 4 while chlorine is introduced to the mixing tee through line 5 from a cylinder, not shown. The mixture is introduced through line 6 to the bottom of primary reactor 7 at point A. Additional butadiene is introduced into the primary reactor at point B, downstream from point A through line 8. The gaseous mixture is removed from the top of reactor 7 through line 9, to secondary reactor 10. The gaseous effluent from reactor 10 is removed through line 11 to scrubber-condenser 12, from which dichlorobutenes are removed at point C as a liquid. Excess butadiene, which is removed from scrubber-condenser 12 at point D, is recirculated to the preheater through line 13, and make-up butadiene is supplied through line 14. Cooling is accomplished in the scrubber-condenser 12 by means of the heat exchanger 12a. BDN indicates butadiene lines.

Temperature within reactor 7 will vary along the reactor's length, generally increasing with the distance from the chlorine-butadiene injection point. The temperature may increase, for example, from about 115° C. at point A to over 200° C. at the top of the reactor. Assume that the temperature in reactor 7 has reached about 200° C. at point B. At this point, only a portion of chlorine, say, one-half of total chlorine, has reacted. Butadiene at 68° C. is now injected at point B, bringing the reactor temperature immediately downstream from point B to 160° C. However, as the remaining chlorine continues to react, the reaction temperature increases further to about 200° C. at the top of reactor 7, where a conversion of about 90% has been reached. Further reaction, accompanied by temperature increase, takes place in the connecting line 9, so that at the entrance to reactor 10 a temperature of 210° C. is reached, and the conversion level is 96%. Reactor 10, in which only about 4% of dichlorobutenes is formed, operates within a narrow temperature gradient, for examle, from 210° C. at the top to 215° C. at the bottom.

The molar ratio of butadiene to chlorine in the feed mixture must be at least 3:1 to avoid formation of higher chlorination products, but not over 30:1 to assure a rapid, exothermic reaction in the initial stage. The preferred ratio is 4:1 to 10:1. The total amount of butadiene, both in the feed mixture and added separately, is such that the mole ratio of butadiene to chlorine preferably is not over 50:1. Larger amounts of butadiene may be uneconomical. While there is no limitation as to the number of butadiene injection points along reactor 7, there is little to be gained by having more than ten such points. To provide efficient cooling, butadiene should preferably be introduced into reactor 7 at a temperature of about 35°–75° C. The amount of butadiene added at each point should not be so large that excessive cooling would take place because of the danger of side reactions in liquid phase which would lower the yield of dichlorobutenes. Preferably butadiene is introduced at a single point, as shown in the drawing, where the reaction temperature upstream of its addition point is about 200°–230° C., the amount of butadiene being sufficient to bring the temperature to about 135°–165° C., while assuring that the temperature at the exit from reactor 10 does not exceed 250° C. Typically, the butadiene inlet may be located at a distance 13-24% of the length of reactor 7 from point A or about 7-12% of the combined lengths of reactors 7 and 10, not including the length of line 9, from point A. (The diameter of line 9 is much smaller than the diameter of reactors 7 and 10, only about 0.04-0.06 of the latter.) If butadiene is introduced at more than one point, the temperature rise between successive points will be smaller, and the temperature along the reactor will be more uniform. However, single butadiene addition point is preferred because a sufficient yield improvement is attained, without requiring a complicated feed rate control system. For practical purposes, whatever the number of butadiene injection points along reactor 7, the temperature of the added butadiene at each point should preferably be about 100°-200° C. below the reactor temperature at that point. The number and location of butadiene addition points can be easily selected on the basis of temperature measurements along the reactor.

The temperature in the reactors depends on the one hand on the amount of heat evolved in the course of the exothermic chlorination reaction and on the other hand on the cooling effect of butadiene. In the initial state of the reaction, the temperature will be close to that of the incoming chlorine-butadiene mixture, say 90°-115° C. As the reaction progresses, and the proportion of dichlorobutenes in the mixture reaches about 1 mole percent, the reaction temperature increases and can be readily maintained through the remainder of the reaction within the desired 130°-250° C. A temperature zone below 130° C. will be present only in the initial, very small portion of the primary reactor; for example, between points A and E of reactor 7 on the drawing.

The improved process of this invention can result in yield improvement of about 2% as compared with the process of British Pat. No. 1,290,607. On industrial production scale, this improvement can produce annual savings of several million dollars. If, on the other hand, one were interested in an increase in reactor capacity, rather than in yield improvement, this increase would amount to about 20% without major modification of existing equipment.

As an additional, and equally important advantage, this invention permits a considerable saving of energy. Because only a portion of butadiene must be preheated, instead of all butadiene, as in prior art processes, the amount of steam required for preheater 3 can be reduced in half. For an industrial operation, this results in a saving per reactor pair of about 140 BTU/lb. dichlorobutenes produced. The amount of energy required for cooling recycle butadiene can be reduced by about 20%.

This invention is now illustrated by the following examples of certain preferred embodiments thereof.

EXAMPLE 1 (Comparative)

An adiabatic reaction system comprising a primary reactor, a secondary reactor, and a scrubber-cooler system as described in the examples of British Pat. No. 1,290,607 is employed. The two reactors are nickel-clad tubes of equal dimensions, have a total volume of 1.98 cubic meters (70 cu. ft), and together contain a reaction zone having a total length-to-diameter ratio of 30:1. Reactor pressure is preferably maintained at approximately 4 kg/cm$^2$ during the course of the reaction. If the pressure is allowed to fall below about 3 kg/cm$^2$, the reactor capacity falls below industrially practical limits. A steady state continuous reaction system is maintained by feeding makeup and recycled butadiene in the total amount of 972 kilograms per hour (18.0 kg-moles/hr) mixed with 90.9 kilograms per hour (1.28 kg-moles/hr) of chlorine to the bottom of the primary reactor at a temperature of about 114° C. The reaction stream at the scrubber-cooler inlet has a temperature of about 213° C. and dichlorobutenes are obtained in 95.1% yield based on chlorine.

EXAMPLE 2

In this example, the process is carried out according to the process of this invention, as illustrated in the drawing. The same reactor is used as in Example 1. Four hundred and eighty-four (484) kg/hr of butadiene (8.96 kg-moles/hr) mixed with 90.9 kg/hr of chlorine (1.28 kg-moles/hr) are fed at about 114° C. to the bottom of the primary reactor, and at a point above the bottom of the primary reactor by a distance equal to 10% of the total length of both the primary and secondary reaction zones, 513 kg/hr of butadiene (9.50 kg-moles/hr) at a temperature of 68° C. is injected through the wall of the reactor into the reaction mixture. Immediately upstream of the butadiene injection point, the temperature of the reaction mixture is about 211° C. The reactor effluent at the inlet to the scrubber-cooler has a temperature of about 184° C. and the yield of dichlorobutenes based on chlorine is 96.9%.

EXAMPLE 3 (Comparative)

Example 1 is repeated with a mixture of 995 kg/hr of butadiene (18.4 kg-moles/hr) and 127 kg/hr of chlorine (1.79 kg-moles/hr), which is fed to the bottom of the primary reactor. The temperature mixture at the inlet to the scrubber-cooler has a temperature of about 245° C. and yields dichlorobutenes in 92.8% yield based on chlorine.

EXAMPLE 4

Example 2 is repeated by feeding a mixture of 580 kg/hr of butadiene (10.7 kg-moles/hr) and 127 kg/hr of chlorine (1.79 kg-moles/hr) at 114° C. to the bottom of the primary reactor and 417 kg/hr of butadiene (7.72 kg-moles/hr) of about 68° C. to the point above the bottom of the primary reactor. The temperature of the reaction mixture immediately upstream of the point of injection of the butadiene is about 220° C. The temperature of the reactor effluent at the scrubber-cooler inlet is about 220° C. and the dichlorobutenes obtained represent a 94% yield based on chlorine. Comparisons of Example 2 with Example 1 and of Example 4 with Example 3 illustrate the improved yields afforded by the invention at equivalent total reactant feed rates.

EXAMPLE 5

The primary reactor used in Example 1 is modified to permit butadiene to be injected into the reaction zone at points above the bottom of the reactor by distances equivalent to 2%, 6%, 14% and 36% of the total length of the primary and secondary reaction zones. A mixture of chlorine and butadiene at about 160° C. is fed to the bottom of the reactor at rates of 90.9 kg/hr (1.28 kg-moles/hr) and 691 kg/hr (12.8 kg-moles/hr), respectively. At the injection points above the bottom of the reactor, butadiene is fed at about 68° C. at rates, respectively of 179 kg/hr (3.31 kg-moles/hr), 221 kg/hr (4.09 kg-moles/hr), 241 kg/hr (4.47 kg-moles/hr) and 255 kg/hr (4.72 kg-moles/hr). Immediately upstream of each injection point, the temperature of the reaction mixture is about 180° C. At the inlet to the scrubber-cooler, the reactor effluent temperature also is about 180° C. and the yield of dichlorobutenes is 97% based on chlorine.

EXAMPLE 6

The primary reactor of Example 1 is modified to permit butadiene to be injected into the reaction zone at points above the bottom of the reactor by distances equivalent to 3.2%, 4.3%, 6.2%, 9.4% and 16.4% of the total length of the primary and secondary reaction zones. Pressure in the reactors is maintained at approximately 4.07 kg/cm$^2$ (4.2 atm) during the course of the reaction. Chlorine and butadiene are mixed and fed at about 120° C. to the bottom of the reactor at rates of 107.9 kg/hr (1.52 kg-moles/hr) and 328.2 kg/hr (6.08 kg-moles/hr), respectively. At the injection points above the bottom of the reactor, butadiene is fed as a liquid at about 38.9° C. at rates, respectively of 40.8 kg/hr (0.76 kg-mole/hr), 46.3 kg/hr (0.86 kg-mole/hr), 52.5 kg/hr (0.97 kg-mole/hr), 59.5 (1.10 kg-moles/hr), and 67.5 kg/hr (1.25 kg-moles/hr). Immediately upstream of each injection point the temperature of the reaction mixture is about 200° C. At the inlet to the scrubber-cooler, the reactor effluent temperature is about 185° C. and the yield of dichlorobutene is 97.2% based on chlorine.

EXAMPLE 7 (Comparative)

The total amounts of chlorine and butadiene are the same as in Example 6, except that all of butadiene and chlorine are mixed in vapor phase before being introduced into the reactor, which is the unmodified reactor of Example 1. The temperature of the vapor feed is about 120° C., and the temperature of the exiting gas is over 300° C. The product yield is only 88.6%.

I claim:
1. An improved process for the continuous chlorination in vapor phase of butadiene to a mixture of dichlorobutenes, the process comprising the following steps:
 1. premixing chlorine with a portion of the total butadiene, the mole ratio of butadiene to chlorine in the mixture being at least 3:1 but no more than 30:1, and the temperature of the mixture being at least 90° C. but no more than 200° C.;
 2. continuously introducing the chlorine-butadiene mixture at one end of a tubular reactor maintained above 90° C., while introducing the remainder of butadiene into the reactor at at least one point downstream from the injection point of the chlorine-butadiene mixture, the temperature of butadiene at each injection point being lower than the temperature of the reacting mixture at that point, both the temperature and the volume of this additional butadiene being adequate to prevent the internal temperature in the reactor from exceeding about 250° C. or falling downstream from any butadiene injection point below about 130° C.; and
 3. recovering dichlorobutenes from the reactor effluent.

2. The process of claim 1 wherein the mole ratio of total butadiene to chlorine is at most about 50:1.

3. The process of claim 2 wherein the mole ratio of butadiene to chlorine in the mixture being fed to the reactor is 4:1 to 10:1.

4. The process of claim 1 wherein the additional butadiene is introduced into the reactor at only one point, the temperature of the reacting mixture at that point being about 200°-230° C.

5. The process of claim 4 wherein the temperature of the additional butadiene is about 35°-75° C., the amount of the additional butadiene being sufficient to bring the temperature to about 135°-165° C.

6. The process of claim 1 wherein the additional butadiene is introduced into the reactor at two or more points, the temperature of the additional butadiene being about 100°-200° C. below the temperature of the reacting mixture at each addition point.

7. The process of claim 1 wherein the tubular reactor is divided into a primary reactor and a secondary reactor connected with each other in series.

8. The process of claim 7 wherein the additional butadiene is introduced into the reactor at only one point located at a distance of about 13-24% of the length of the primary reactor from the inlet of butadiene-chlorine mixture or 7-12% of the combined length of both reactors from said inlet, the length of any connecting piping between the primary and secondary reactors being disregarded for this purpose.

9. The process of claim 1 wherein the additional butadiene is introduced into the reactor at one point.

* * * * *